United States Patent [19]

Elliott

[11] Patent Number: 5,735,819
[45] Date of Patent: Apr. 7, 1998

[54] TEAR-APART MEMBER FOR POSITIONING A GROMMET CARRIED THEREON

[75] Inventor: Gregory D. Elliott, Hagerstown, Ind.

[73] Assignee: Cook Incorporated, Bloomington, Ind.

[21] Appl. No.: 692,057

[22] Filed: Aug. 2, 1996

[51] Int. Cl.$^6$ .................................................. A61M 25/06
[52] U.S. Cl. ............................................. 604/161; 604/160
[58] Field of Search ................................. 604/158–165, 604/169, 171, 174, 175, 180, 263, 264, 280

[56] References Cited

U.S. PATENT DOCUMENTS

| | | | |
|---|---|---|---|
| Re. 31,855 | 3/1985 | Osborne. | |
| 4,327,722 | 5/1982 | Groshong et al. | 604/169 |
| 4,411,654 | 10/1983 | Boarini et al. | 604/161 |
| 4,412,832 | 11/1983 | Kling et al. | 604/161 |
| 4,581,025 | 4/1986 | Timmermans | 604/160 |
| 4,613,329 | 9/1986 | Bodicky. | |
| 4,772,266 | 9/1988 | Groshong | 604/160 |
| 4,950,259 | 8/1990 | Geary et al. | 604/175 |
| 5,065,466 | 11/1991 | Thomas et al. | |
| 5,141,497 | 8/1992 | Erskine | 604/160 |
| 5,167,634 | 12/1992 | Corrigan, Jr. et al. | 604/160 |
| 5,250,033 | 10/1993 | Evans et al. | 604/160 |
| 5,330,438 | 7/1994 | Gollobin et al. | |

FOREIGN PATENT DOCUMENTS

| | | | |
|---|---|---|---|
| 9304726 | 3/1993 | WIPO | 604/161 |

Primary Examiner—Michael Buiz
Assistant Examiner—Kevin Truong
Attorney, Agent, or Firm—Richard J. Godlewski

[57] ABSTRACT

A grommet positioning device 10 includes a positioning member 16, such as a sheath 28, carrying an elastic anchor, fastener or grommet 14 thereon. The grommet 14 is preferably composed of silicone and has a predefined, unstressed interior diameter. The positioning member 16 includes a portion 25 in contact with the grommet, the portion 25 having an outer diameter at least equal to the predefined, unstressed interior diameter of the grommet 14. The positioning member 16 is capable of being split or torn apart along at least the portion 25, so as to release the grommet 14 from the member 16 and allow it to be fixed in position along an object such as a catheter 12. The interior diameter of the grommet 14 is chosen to preclude closure or blockage of the catheter 12 when the grommet 14 is positioned on it. The positioning member 16 is preferably configured as a sheath 28 composed of molecular oriented PTFE, capable of being split along its entire length, and includes pull tabs 46 for causing such splitting. The grommet 14 can include shoulders 44 for assisting securement of the grommet 14 to its environment of use as desired, for example, adjacent to the body 20 of a patient being catheterized. A catheterization apparatus 56 includes a catheter 12 carrying the grommet positioning device 10 on it.

22 Claims, 8 Drawing Sheets

TEAR-APART MEMBER FOR POSITIONING A GROMMET CARRIED THEREON

TECHNICAL FIELD

This invention relates generally to tear apart devices; more particularly, to tear apart devices for positioning grommets, anchors and the like; and, especially, to such tear apart positioning devices that are useful in medical procedures.

BACKGROUND OF THE INVENTION

Catheters have long been used for a wide variety of medical procedures. Such procedures have included the intravenous administration of nutrient fluids, the delivery of whole blood or blood products, the sampling of blood, the administration of chemotherapeutic agents or other drugs, among a host of other procedures. It is often important to such uses that the distal end of the catheter, positioned within the patient, be precisely maintained in a specific location in the patient for an extended period of time.

A variety of ways are known for fixing the position of a catheter inserted in a patient. While generally successful for their intended purposes, such techniques are often subject to drawbacks. For example, the catheter may simply be tied by sutures to the skin of the patient, or to surgical drape or bedding adjacent to the access site at which the catheter is inserted into the patient's body. Unfortunately, unless such suturing is carried out with care, the sutures themselves may compress, breach or collapse the catheter, making it useless for its intended purpose.

The attachment of intermediate articles such as fasteners, anchors, hubs, fittings, grommets or the like to the catheter can mitigate this drawback. Such intermediate articles usually surround or encircle the catheter, and suturing the articles rather than the catheter avoids damage to the catheter. Intermediate articles of this type are sometimes collectively referred to as "grommets."

The use of some preaffixed grommets can require that the distal end of the catheter be cut to its useful, specific length only after the catheter wire guide is inserted into and withdrawn from the patient. However, cutting the distal end of a catheter is often times not available since many catheters have preformed distal tips or the distal portion of the catheter is of a different material or construction. Additionally, the need to introduce the wire guide a second time to allow introduction of the catheter into the patient or actually cut the catheter tip undesirably increases the time, risk and cost of catheterization.

The use of a grommet attached only after introduction of the catheter into the patient can be subject to different drawbacks. Arrow Corporation, for example, distributes a split, winged grommet with a hard plastic clip for securing the grommet to a catheter. While this device appears to be useful for its intended purpose, the high flexibility of many catheters makes it difficult to attach some clip-type grommets without risking compression, collapse or breach of the catheter by the grommets themselves. Since the purpose of a grommet is to provide a fixed position along the catheter for securement to the environment, it should be apparent that it often would be difficult to slide a clip-type grommet in order to change its position along the catheter.

U.S. Pat. No. 4,613,329 (Bodicky, Sep. 23, 1986) discloses a catheter placement device which partly addresses this last concern. The device disclosed in the patent includes an elastomeric grommet compressed against a catheter, the grommet having a flange engageable with the catheter. The flange provides relatively high resistance to proximal movement of the catheter, but only relatively low resistance to distal movement of the catheter. While this serves to deter the inadvertent withdrawal of the catheter from the patient, is would also seem possible that the catheter could be inadvertently pushed distally or inwardly beyond its desired location. Moreover, the disclosed device is of relatively complex construction for the function it performs.

One type of grommet, known as a Roko-type grommet, comprises a plurality of elastic rings, more particularly, a central ring encircling the catheter, and the other rings serving as sites for attaching sutures. During use, the central ring is manually spread wide by hemostats so that the grommet can be slid along the catheter. Such manipulation becomes difficult with grommets suited to catheters of small diameter. Smaller diameter catheters are desirable, of course, because of the reported correlation of catheter size with the formation of blood clots; larger diameter catheters appear to have a greater tendency to promote clots, and catheter diameter may be more important than catheter composition in the promotion of clots.

It would be highly desirable to have a grommet positioner which allowed a grommet to be selectively positioned along the length of a catheter without requiring the use of hemostats or another rigid tool for spreading the grommet wide while moving it along the catheter. It would also be desirable to have a grommet positioner which did not require the repeated removal of the wire guide once inserted into the patient, or the cutting of the catheter to any specific length. It would further be desirable to have a grommet positioner which was of simple and relatively inexpensive construction, which could be packaged with and sterilized with the specific catheter it is intended for. Finally, it would be desirable to have a grommet positioner useful for positioning grommets on objects besides catheters.

SUMMARY OF THE INVENTION

The foregoing problems are solved and a technical advance is achieved in an illustrative grommet positioning device, as well as an illustrative catheterization apparatus incorporating the grommet positioning device. Applicant has discovered a way to position an elastic grommet at any desired position along an object, for example, such as a catheter. More particularly, applicant has discovered that a tear apart or splittable positioning member can be employed to carry the elastic grommet on it; when the positioning member is torn apart or split, the grommet is released from the positioning member and automatically positioned at a desired location.

A key feature of the invention is that the portion of the positioning member in contact with the elastic grommet has a diameter at least equal to the predefined, unstressed interior diameter of the grommet. "Predefined, unstressed interior diameter" means the interior diameter possessed by the grommet when it is free of the positioning member or any other object, that is, its free or natural diameter. "Diameter" merely means a dimension across the interior of the grommet; the various constituents of the invention may, but need not necessarily be, circular in cross-section.

The elastic grommet is preferably retained on the positioning member solely by friction or elastic compression, so that when the grommet is released from the positioning member, it collapses upon the object on which it is to be positioned. The positioning member is preferably configured as a sheath, sleeve, tube or the like (collectively referred to herein as a "sheath"), and can advantageously be constructed of a low friction material such as PTFE, to aid movement of the positioning member and grommet along the object.

The word "grommet" is used herein in its broadest sense, and includes items such as grommets, fasteners, anchors, hubs, fittings and the like, all employed as intermediates for protecting, connecting and/or securing other objects. While the grommet positioning device of the present invention finds particular utility when used in conjunction with a catheter or other medical devices, it is, of course, useful with a variety of other objects. Also, the word "grommet" encompasses a DACRON fabric cuff of the type which becomes anchored by the ingrowth of tissue. Also encompassed are similar devices possessing sufficient elasticity to contract upon the catheter or other object, or to achieve an interference fit with the catheter or other object, when released from the positioning member. Of course, the grommet can alternatively be treated to prevent tissue ingrowth and/or to guard against infections, fungus, thrombus, bacteria and the like.

In a first aspect, then, the present invention is directed to a device for positioning a grommet, anchor, fastener, hub, fitting or the like, collectively referred to as a grommet, comprising an elastic grommet having a predefined, unstressed interior diameter, and a positioning member carrying the grommet thereon, the member including a portion in contact with the grommet. The portion of the positioning member has an outer diameter greater than the predefined, unstressed interior diameter of the grommet, and the member is capable of being torn apart or split along at least the portion so as to release the grommet from the member. The elastic grommet is preferably composed of silicone and can include means such as shoulders, wings, rings, DACRON cuffs or the like for assisting securement of the grommet adjacent to the body of a patient. "Adjacent to" the patient's body includes both to the patient's body itself, and to the environment surrounding the patient's body. The positioning member is preferably configured as a sheath, sleeve tube or the like, and is preferably composed of a low friction material such as PTFE. Most preferably, the positioning member is a sheath composed of molecular oriented PTFE, a material which is the subject of U.S. Pat. No. RE 31,855, owned by the assignee herein. The disclosure of that patent is incorporated in its entirety by reference herein.

In a second aspect, the present invention is directed to a grommet positioning device comprising a specific combination of the preferred elements described above.

In a final aspect, the present invention is directed to a catheterization apparatus comprising a catheter and the grommet positioning device described above.

The present invention provides a grommet positioner which allows a grommet to be easily moved and selectively positioned along the length of a catheter, without requiring the use of hemostats to spread and possibly damage the grommet. The present invention avoids the risks and costs associated with the repeated removal of the wire guide for the catheter, and eliminates the need to cut the catheter to any specific length. The grommet positioner of the present invention is particularly advantageous in that it is of simple and relatively inexpensive construction. Of course, the grommet positioner of the present invention is useful for positioning grommets on objects other than catheters.

BRIEF DESCRIPTION OF THE DRAWING

A better understanding of the present invention will now be had upon reference to the following detailed description, when read in conjunction with the accompanying drawing, wherein like reference characters refer to like parts throughout the several views, and in which.

DETAILED DESCRIPTION

Figure 1:
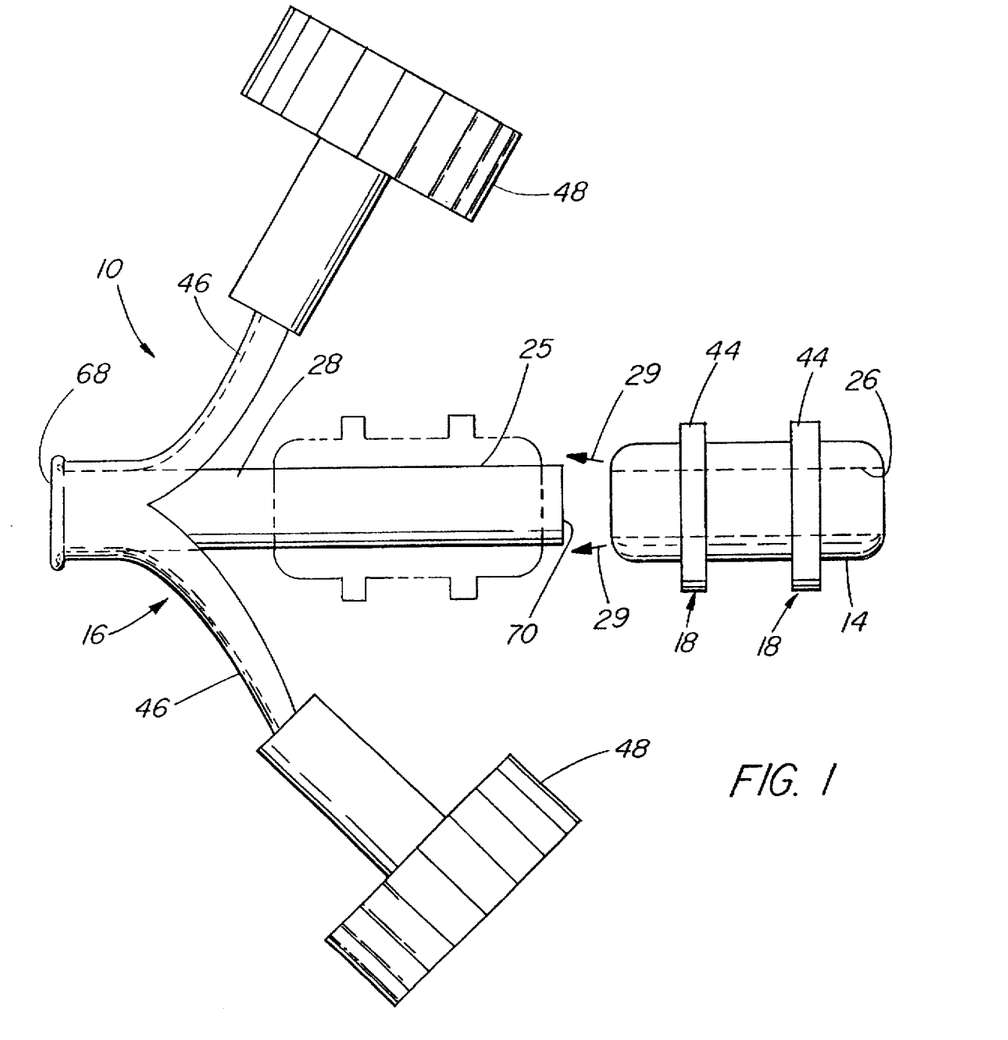
FIG. 1 is a plan view of the preferred embodiment of the grommet positioning device of the present invention.

With reference first to FIG. 1, a device 10 for selectively positioning a grommet on or along an object such as a medical device is thereshown, first comprising a grommet 14 having an interior surface 26 defining a predefined, unstressed interior diameter of the grommet 14. The grommet positioning device 10 also comprises a positioning member 16 carrying the grommet 14 thereon. The positioning member 16 includes a portion 25 in contact with the grommet 14. The portion 25 of the member 16 has an outer diameter at least equal to, and preferably greater than, the predefined, unstressed interior diameter of the grommet 14. The grommet 14 can most easily be placed on the portion 25 of the member 16 by sliding it over the distal end 70 of the member. Such sliding is indicated by arrows 29, which indicate the expansion experienced by the grommet 14 during the sliding. The grommet 14 is preferably positioned closely to the distal end 70 of the positioning member 16, permitting good precision of the position on the object at which the grommet 14 will be fixed.

The positioning member 16 is preferably configured as a sheath 28. The member 16 can also be configured as a sleeve, a tube or the like. Whatever its configuration, however, the positioning member 16 must be capable of being split or torn apart along at least the portion 25 in contact with the grommet 14. Splitting of the portion 25 releases the grommet 14 from the positioning member 16, and thereby deposits the grommet 14 on any object with which the member 16 is engaged. The member 16 preferably can be split or torn apart along its entire length, so as to allow it to be removed transversely from the object on which the grommet 14 is deposited, without having to be slipped off the end of the object.

The positioning member 16 can be constructed in a variety of ways. The member 16 can be splittable along its entire length, or only along the portion 25 in contact with the grommet 14. The member 16 can be composed of scribed or molded PTFE, with thin longitudinal portions susceptible to splitting. When it splits, the member 16 can split into linear pieces, or can split along one or more spirals. The member 16 can be of unitary construction, or can be frangible or breakable, or can comprise a plurality of pieces attached together. Such pieces could be glued together, secured to one another by sonic welding, or otherwise connected. A variety of plastic or synthetic materials are expected to be useful for the composition of the positioning member 16. The member 16 preferably has some degree of flexibility, and is preferably somewhat less flexible than the elastic grommet 14, but may itself be somewhat elastic and expansible. Indeed, the member 16 can itself possess a predefined, unstressed inside diameter smaller than the outside diameter of the object on which the grommet 14 is to be deposited.

Most preferably, however, the positioning member 16 is configured as a sheath 28 composed of molecular oriented PTFE. The sheath 28 is folded upon itself to form a proximal end 68 of the sheath 28 (that is, of the member 16) and has a pair of partial splits forming a pair of pull tabs 46 for splitting at least the portion 25, and preferably the entire sheath 28. A knob 48 is provided on each of the pull tabs 46 for ease of grasping and pulling.

Figure 6A:
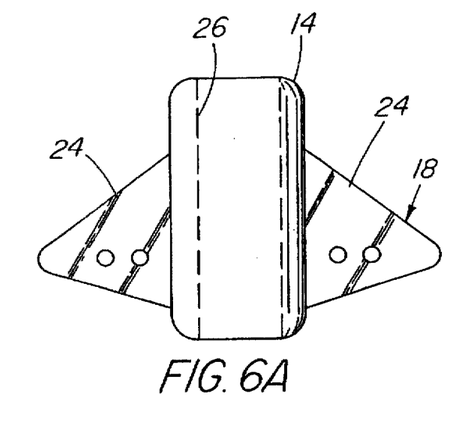
FIGS. 6A, 6B, and 6C are plan views of further preferred embodiments of the grommet positioning device of the present invention.
Figure 6B:
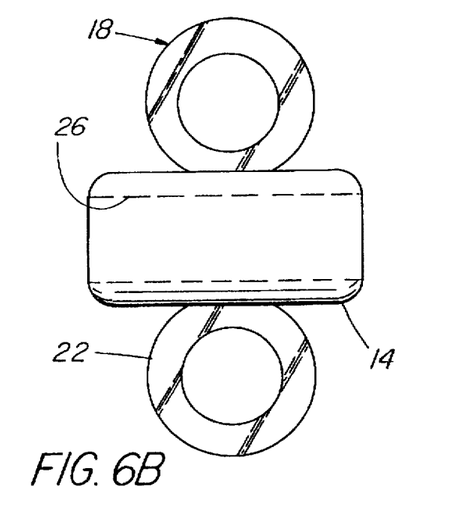
Figure 6C:
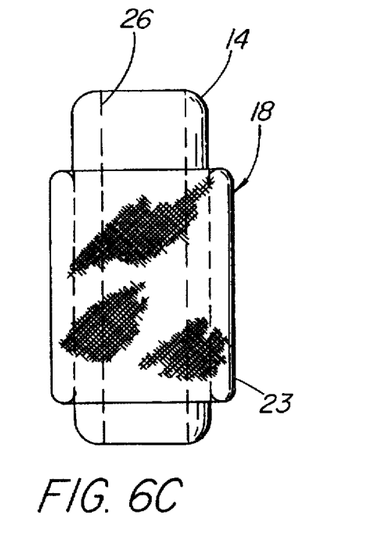

The elastic grommet 14 can also be configured in a variety of ways. While a number of materials are suitable for its composition, the grommet 14 is preferably composed of medical grade silicone. The grommet 14 is shown in FIG. 1 as a hollow cylinder having rounded ends, but this basic shape is merely a convenience. More importantly, the grommet 14 comprises means 18 for assisting securement of the grommet 14 adjacent to the body 20 of a patient. "Adjacent to" the body 20 includes all of: attachment to or in the body 20; attachment to or in the skin 40; and attachment to the environment near the object to which the grommet 14 will be fixed, for example, to dressings or surgical drapes near a catheter access site. The securement assisting means 18 preferably comprises at least one and more preferably a pair of shoulders 44. The shoulders 44 allow a suture to loop about and be tightened about the grommet 14, and prevent the suture from sliding off the grommet 14 during use of the object on which the grommet 14 is to be positioned. Alternatively, the securement assisting means 18 can be configured as at least one and preferably a pair of perforate wings 24 (FIG. 6A), at least one and preferably a pair of rings 22 (FIG. 6B), or a DACRON cuff or sleeve 23 (FIG. 6C) that is affixed to grommet 14 using, for example, a medical grade adhesive.

Figure 2:
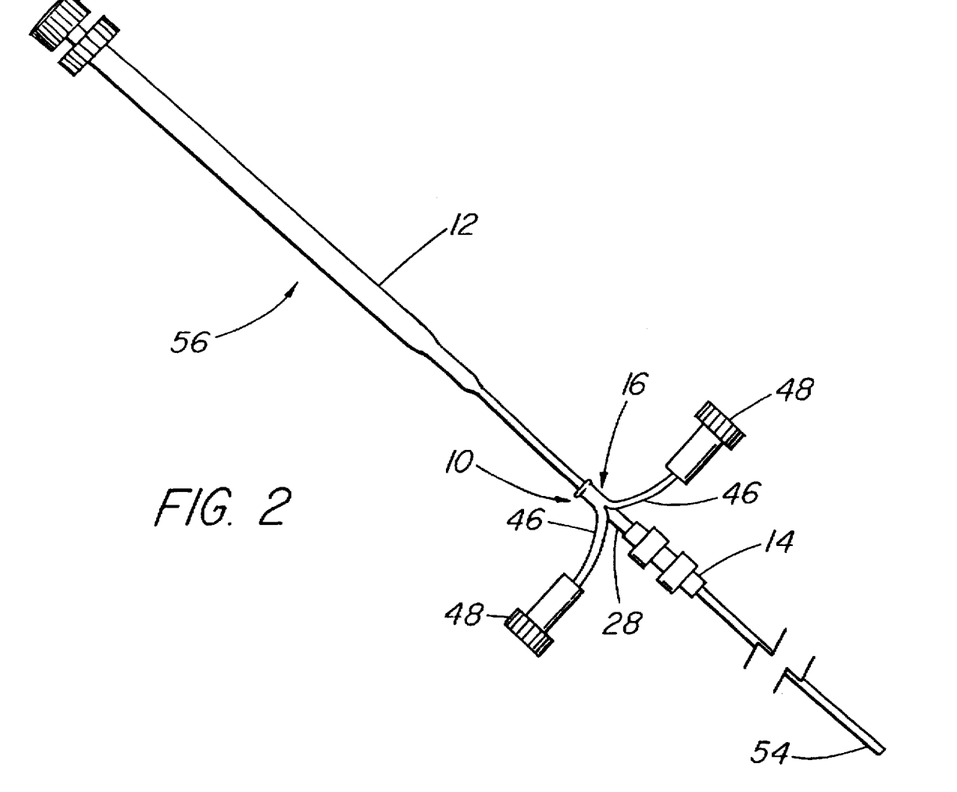
FIG. 2 is a perspective view of the preferred embodiment of the catheterization apparatus of the present invention, incorporating the disclosed grommet positioning device.
Figure 3:
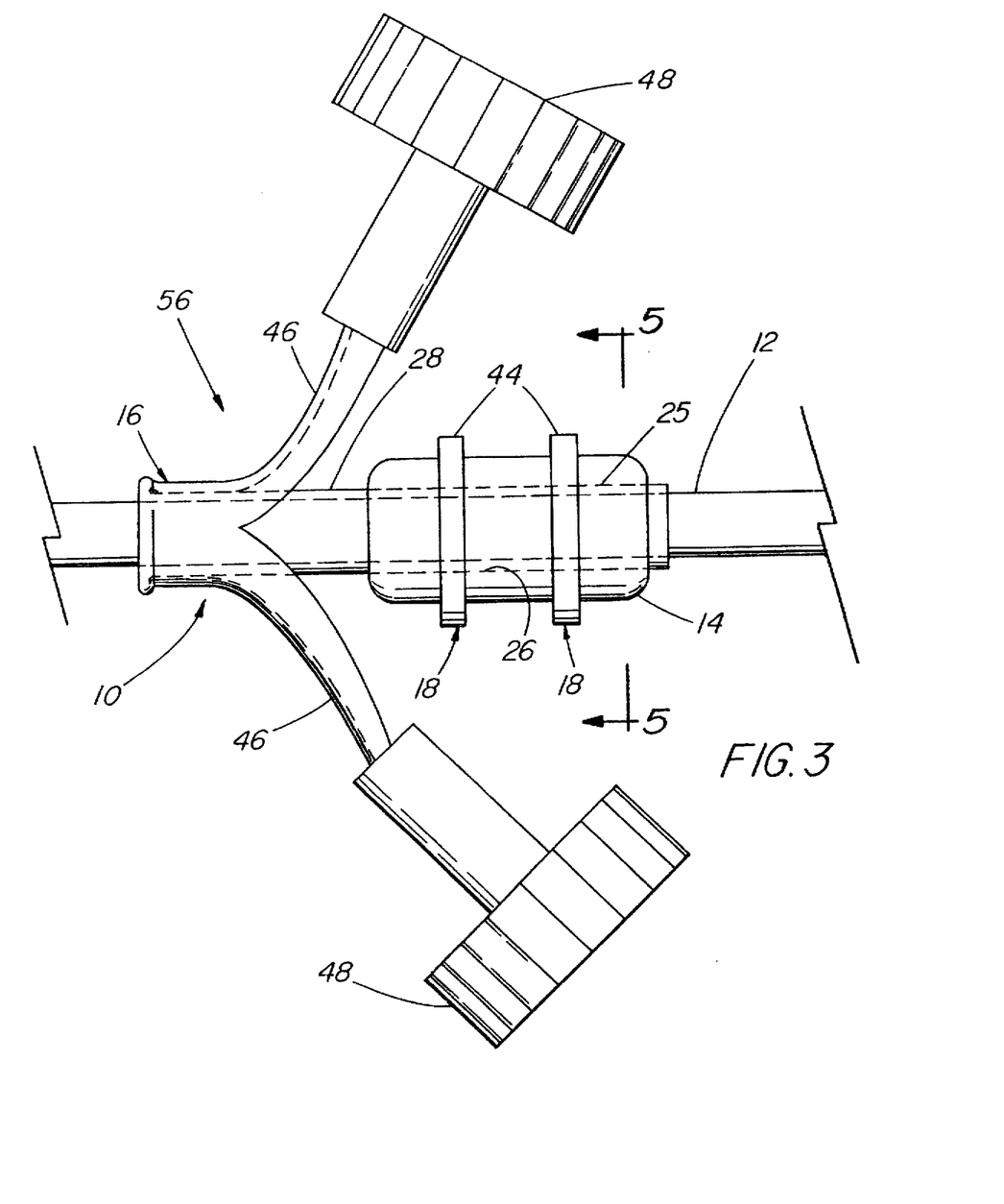
FIGS. 3 and 4 are plan views of a portion of the preferred embodiment of the catheterization apparatus of the present invention.

With reference now to FIGS. 2 and 3, a catheterization apparatus 56 according to the present invention is thereshown and first comprises a catheter 12 receiving the grommet positioning device 10 of the present invention thereon. The catheter 12 can be a single lumen or plural lumen catheter, and is preferably composed of a highly elastic, medical grade silicone. The catheter 12 can be of the type which requires it to be advanced over a wire guide positioned within a patient. Preferably, however, greater advantages are achieved when the catheter 12 is of the type which instead incorporates in its lumen a removable obturator 34 which supports the catheter 12 during its introduction into a patient. The catheter 12 can otherwise be of any conventional or desired construction.

In order to achieve securement of the elastic grommet 14 to the catheter 12 upon release from the positioning member 16, the predefined, unstressed interior diameter of the grommet 14 is about no greater than the outer diameter of the catheter 12, and is preferably slightly less than the outer diameter of the catheter 12. However, the predefined, unstressed interior diameter of the grommet 14 is also sufficiently large to avoid closure, blockage or collapse of the lumen of the catheter 12 when the grommet 14 is deposited on the catheter 12.

Figure 5:
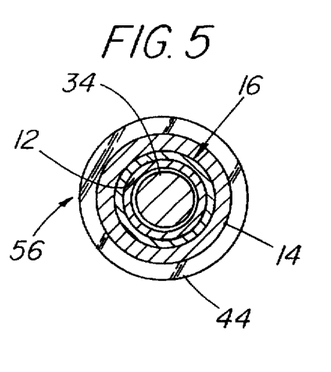
FIG. 5 is a cross-sectional view taken along line 5—5 of FIG. 3.

The catheterization apparatus 56 incorporates the preferred grommet positioning device 10 as disclosed above, that is, the apparatus 56 further comprises an elastic grommet 14 as described, encircling the catheter 12 and being carried by a positioning member 16 received on the catheter 12. The member 16 is preferably configured as a molecular oriented PTFE sheath 28 splittable along its entire length. The member 16 is most easily engaged with the catheter 12 by sliding the distal end 54 of the catheter 12 into the proximal end 68 of the member 16 and completely through the member 16. The member 16 must of course be stiff enough to allow such sliding, but should still be fairly flexible. The resulting overlap of elements is shown in cross-section in FIG. 5.

Figure 4:
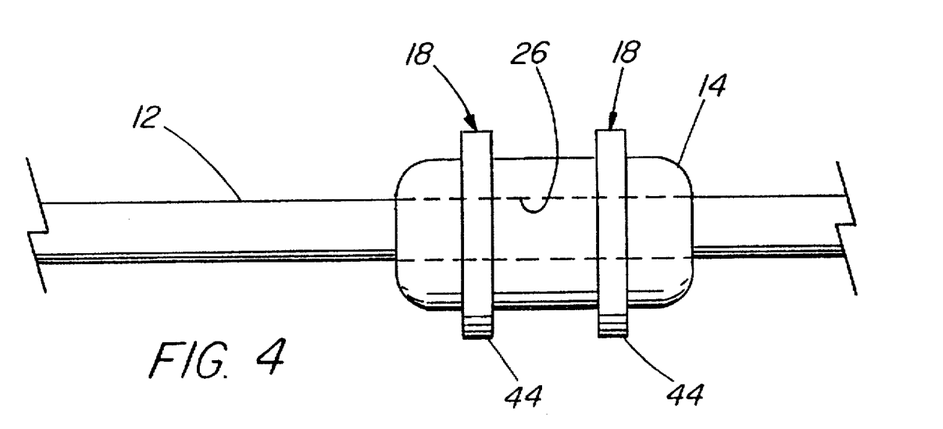

The positioning member 16 of the catheterization apparatus 56 as depicted in FIG. 3 includes a portion 25 in contact with the grommet 14, and the portion 25 has an outer diameter at least equal to the predefined, unstressed interior diameter of the grommet 14, so that the member 16 and grommet 14 are selectively positionable together along the catheter 12. The member 16 is capable of being torn apart or split along at least the portion 25 so as to release the grommet 14 from the member 16 and thereby fix the position of the grommet 14 along the catheter 12. Such fixing can be achieved either by a compression fit of the grommet 14 with the catheter 12, or by an interference fit of the grommet 14 with the catheter 12. This fixing is shown in FIG. 4, and is achieved upon splitting of at least the portion 25 of the positioning member 16.

Accordingly, the catheterization apparatus 56 is preferably characterized in that friction against the catheter 12 by the grommet 14, or compression of the catheter by the grommet 14, is the sole force preventing relative movement of the grommet 14 and the catheter 12, after splitting of the positioning member 16. No suture, adhesive, separate clip or other means is needed to fix the grommet 14 to the catheter 12. Compression of the catheter by the grommet is also limited so as not to collapse or block any of the passages or lumens of the catheter 12.

The catheterization apparatus 56 preferably incorporates other features of the grommet positioning device 10 as disclosed above. For example, the grommet 14 preferably includes the shoulders 44 or other securement assisting means 18 previously described. Similarly, the positioning member 16 preferably comprises the pull tabs 46 for splitting at least the portion 25 of the member 16 in contact with the grommet 14.

Figure 7:
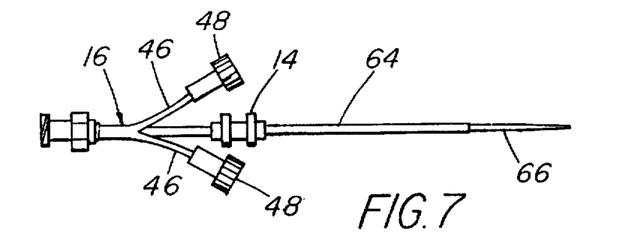
FIG. 7 is a plan view Of another preferred embodiment of the grommet positioning device of the present invention.

Of course, the grommet positioning device 10 incorporated in the catheterization apparatus 56 need not necessarily be carried by the catheter 12 prior to use. Instead, the device 10 can alternatively be part of the dilator assembly employed to enlarge the catheter access site in the skin 40 of the patient. Such an assembly is shown in FIG. 7, in which the positioning member 16 is configured as a molecular oriented PTFE dilator sheath 64 having a conventional dilator 66 passing through it. The grommet 14 is released from the dilator sheath 64 by grasping the knobs 48 and pulling on the pull tabs 46, but is released only after the dilator 66 has been removed from the sheath 64 and the catheter 12 introduced through the sheath 64. In this embodiment, the grommet 14 is typically carried a bit more proximally on the dilator sheath 64 than on the sheath 28 disclosed above, because the dilator sheath 64 must extend for some distance along the dilator 66. This extension may reduce the precision of the positioning achieved in this embodiment.

Use of the device 10 of the present invention for positioning a grommet 14 on an object, such as on a catheter 12, can now be readily understood. Such use is conveniently carried out with a catheterization apparatus like the apparatus 56 described above, in which the grommet positioning device 10 is mounted on the catheter 12 prior to sterilization and packaging by the manufacturer. Alternatively, the device 10 can be packaged separately, and positioned on the catheter 12 by the health care practitioner before use of the catheter 12.

As a preliminary, for the sake of brevity only those aspects of catheterization technique especially pertinent to the use of the grommet positioning device 10 will be addressed in detail. It is presumed that the practitioner is otherwise well familiar with the introduction and positioning of catheters in the body 20 of a patient, for example, in a vessel such as a blood vessel 42. It is also presumed that the practitioner is familiar with the requirements for selecting an appropriate site of access through the skin 40, and for choosing a catheter 12 of suitable diameter. The practitioner should, for example, be aware of the circumstances under which accurate placement of the catheter would require monitoring by ECG, radiography and/or fluoroscopy.

Figure 8A:
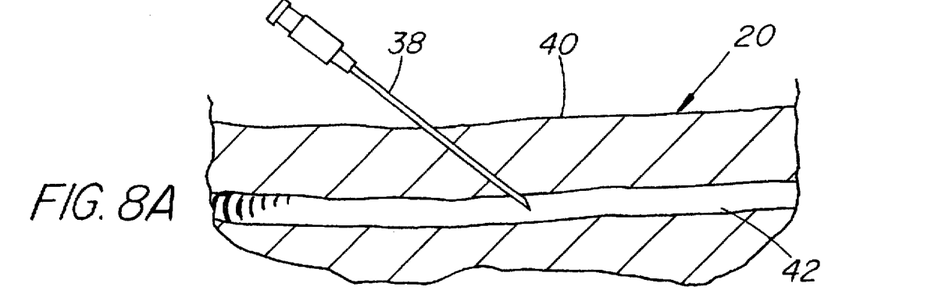
FIGS. 8A through 8J are partial cross-sectional views of the preferred embodiment of the catheterization device of the present invention during use.
Figure 8B:
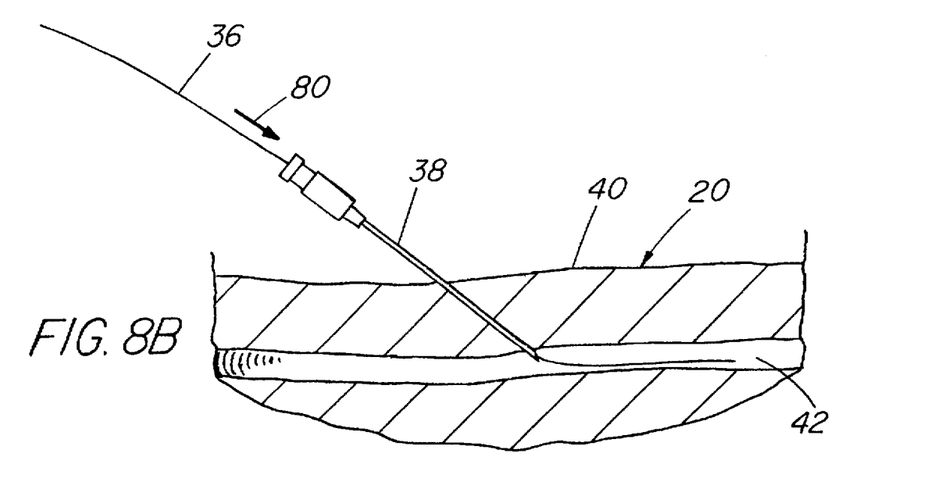
Figure 8C:
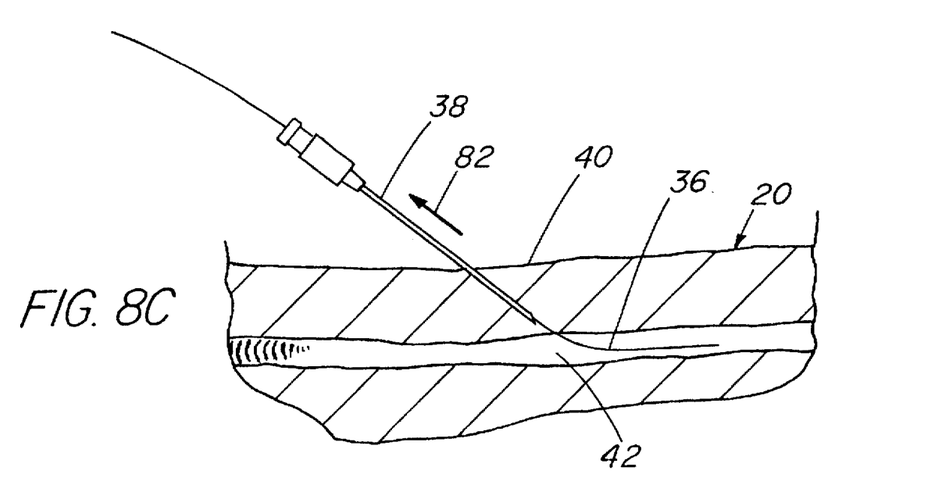

The access site for entry of the catheter 12 on the skin 40 of the patient's body 20 must first be prepared and maintained in a manner consistent with standard procedures for the particular catheterization being performed. As shown in FIG. 8A, once the access site is prepped, a thin wall percutaneous entry needle 38 is introduced into the blood vessel 42. Next, as shown in FIG. 8B, a wire guide 36 is introduced (in the direction of arrow 80) through the needle 38 and advanced fifteen to twenty centimeters into the blood vessel 42. Fluoroscopic guidance of such advance is recommended. Once the wire guide 36 is suitably advanced, the needle 38 is withdrawn from the skin 40 (in the direction of arrow 82 in FIG. 8C) and proximally withdrawn from the wire guide 36, leaving the wire guide 36 in place. The resultant puncture in the skin 40 may be enlarged with a scalpel blade or other means, if necessary.

Figure 8D:
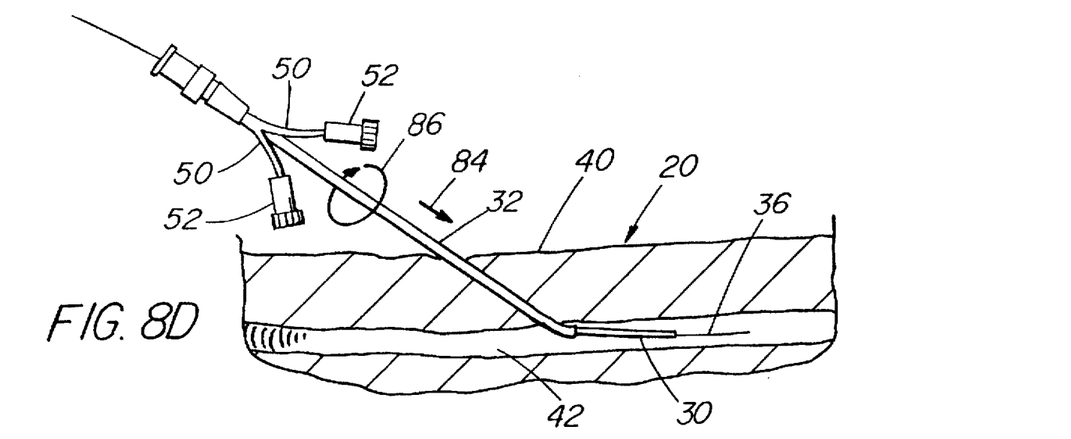

As shown in FIG. 8D, a conventional dilator 30 and a dilator sheath 32 containing the dilator 30 are next introduced together over the wire guide 36 and advanced through the skin 40 in the direction of arrow 84 until the distal tip of the dilator 30 lies fully within the blood vessel 42. Rotation of the dilator 30 and sheath 32 in the direction of arrow 86 will likely facilitate their advancement.

Figure 8E:
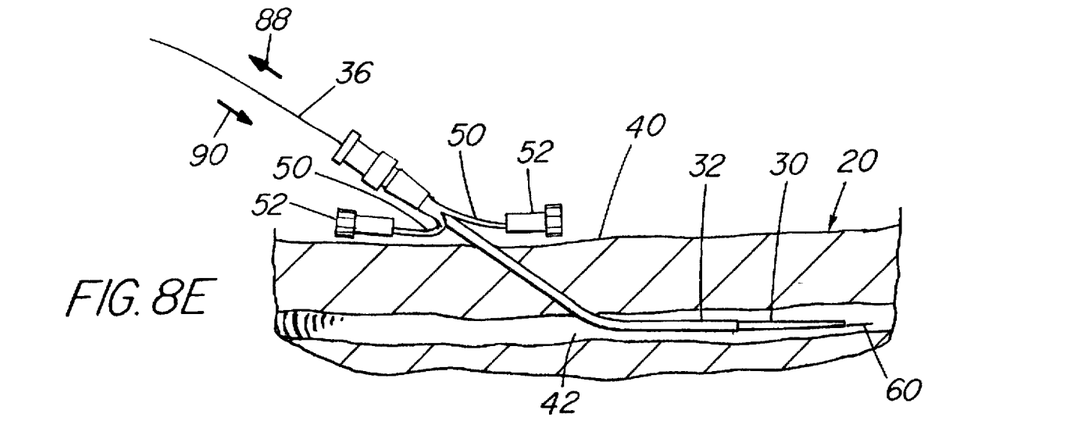

Presuming that the catheter 12 is of suitable length, the wire guide 36 as shown in FIG. 8E, can now be removed by withdrawing it in the direction of arrow 88. Alternatively, if for some reason the catheter 12 must be cut to a particular length, the wire guide 36 can first be advanced in the direction of arrow 90 until its tip 60 reaches the location ultimately desired for the distal catheter tip (monitored by fluoroscopy). The length of the wire guide 36 can then be marked by clamping with forceps at the dilator 30, withdrawn in the direction of arrow 88, and the catheter 12 trimmed to the appropriate length. It is an advantage of the preferred embodiments of the present invention, however, that such measuring and cutting is avoided. Of course, if the catheter 12 is of a type not containing an obturator, the wire guide 36 should not be removed at this time, but left in place to guide the later introduction of the catheter 12.

Figure 8F:
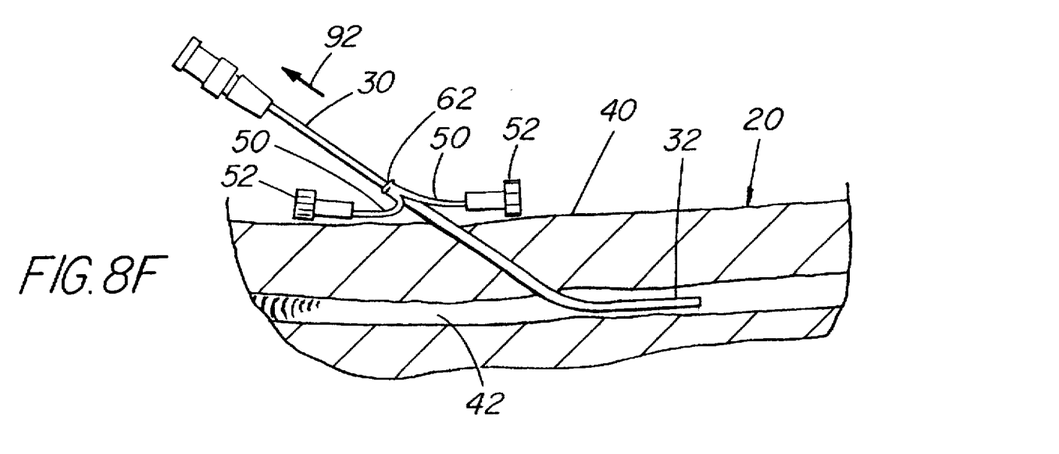

Next, as shown in FIG. 8F, the dilator 30 is removed from the patient in the direction of arrow 92 while leaving the dilator sheath 32 in place. The thumb or finger should be placed over the proximal end 62 of the dilator sheath 32 after removing the dilator 30 and wire guide 36 to prevent the inadvertent aspiration of air through the dilator sheath 32 before introduction of the catheter 12 through it.

Figure 8G:
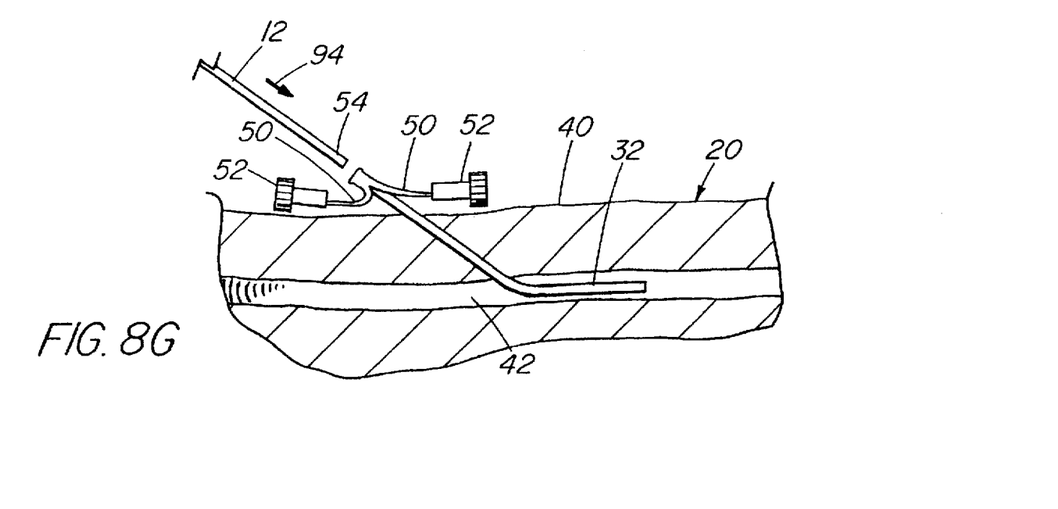
Figure 8H:
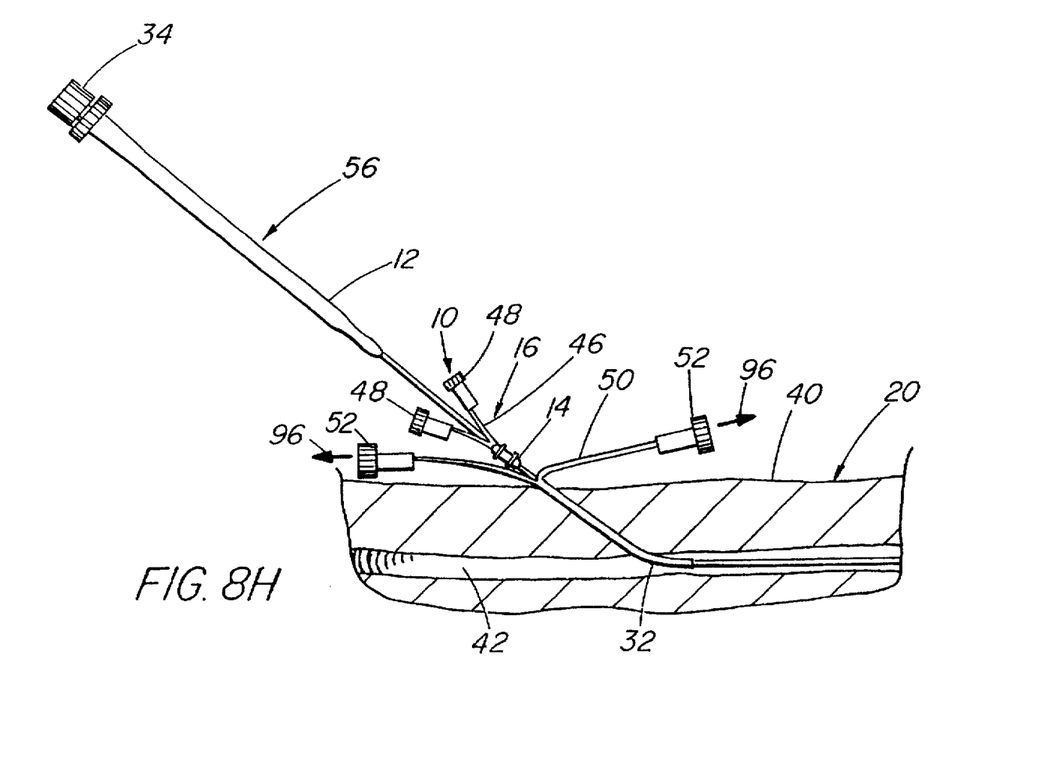
Figure 8I:
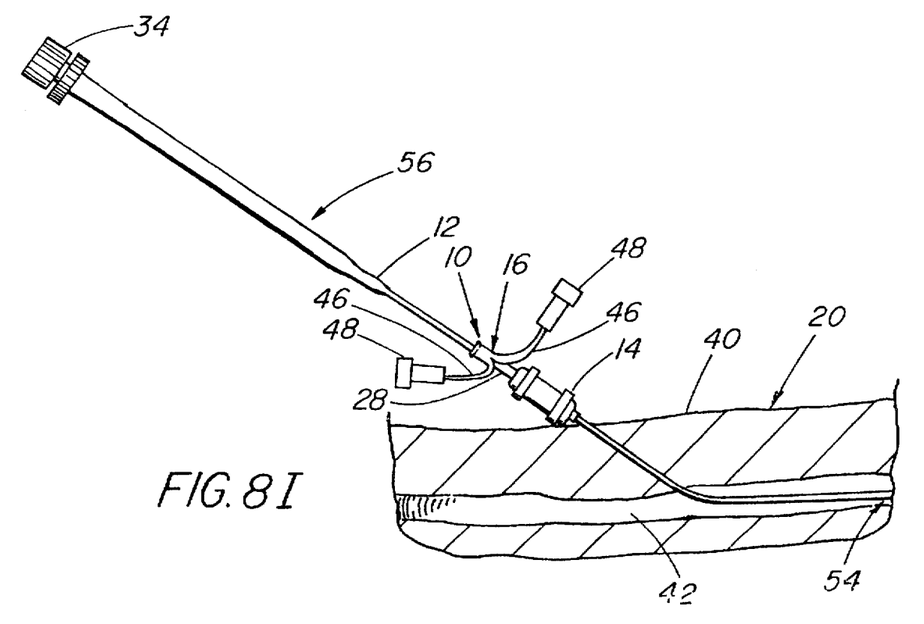
Figure 8J:
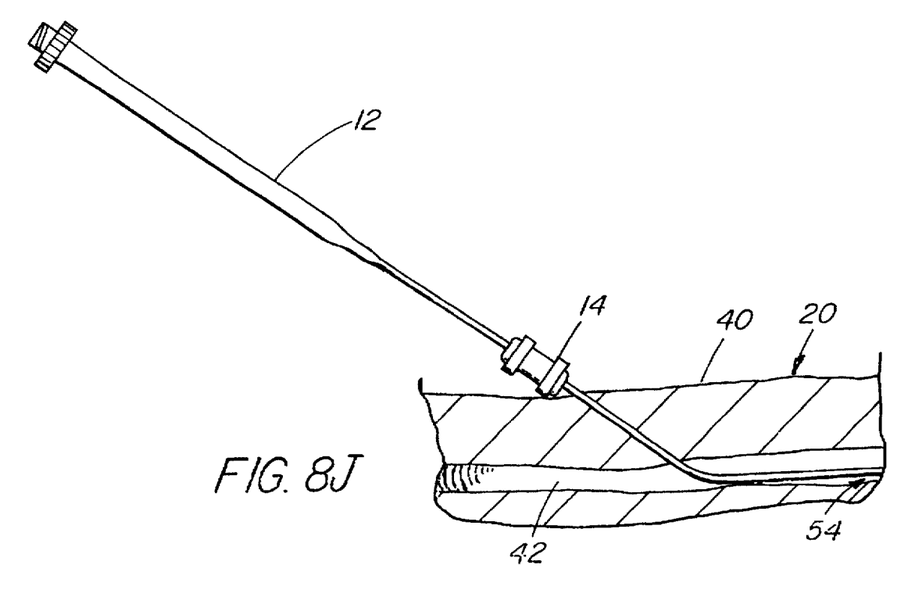

The distal tip 54 of the catheter 12 is then introduced into the dilator sheath 32, and the catheter 12 advanced in the direction of arrow 94 (FIG. 8G) until the distal tip 54 of the catheter 12 is positioned at the desired location within the blood vessel 42. Once the catheter 12 achieves the desired position, the dilator sheath 32 is removed by pulling the knobs 52 on pull tabs 50 in the direction of arrows 96 (FIG. 8H), upward and outward at the same time, to peel or tear the dilator sheath 32 away from the catheter 12 while maintaining the catheter 12 in its desired position. As shown in FIG. 8I, this leaves the grommet positioning device 10 in position on the catheter 12 adjacent to the body 20 of the patient. The positioning device 10 can then be moved along the catheter 12 to position the grommet 14 at any exact position desired. The tabs 46 on the positioning member 16 (exemplified by the sheath 28) are then pulled by grasping on the knobs 48, and drawn upward and outward at the same time, to simultaneously release the grommet 14 from the member 16 and remove the positioning member 16 from the catheter 12, automatically positioning and fixing the grommet 14 on the catheter 12. The obturator 34 is then removed from the catheter 12. (Alternatively, if the catheter 12 did not incorporate the obturator 34, the wire guide 36 would be removed at this time.) In either case, the resulting arrangement is shown in FIG. 8J.

The catheter 12 can now be fixed in position by suturing or otherwise securing the grommet 14 adjacent to the body 20 of the patient, for example, adjacent to the catheter access site, and dressed in any standard fashion. The grommet 14 can be sutured to the skin 40 of the patient or can be sutured to a surgical drape or dressing (not shown) near the access site. It is recommended that the position of the distal catheter tip 54 be verified by radiography at this time. It is also recommended that lumen patency be confirmed prior to use, for example, by the free aspiration of venous blood through the catheter 12. If blood cannot be freely aspirated, the position of the distal catheter tip 54 should be immediately reevaluated by the health care practitioner. If the catheter 12 is not to be used immediately after the confirmation of lumen patency, it is recommended that the lumen be maintained by a continuous drip of saline or heparinized saline, or be locked with a suitable heparinized saline solution. Heparin lock should be reestablished after every use of the catheter 12, or after every eight hours if the catheter 12 remains unused. Normal lumen flushing procedures should of course be performed before use of the catheter 12 for infusion or sampling, or between the sequential administration of different infusates. Again, it is presumed that the health care practitioner is familiar with proper medical practices in this regard.

It should be clear from the foregoing that the present invention provides a grommet positioning device which allows a grommet to be easily moved and selectively positioned anywhere along the length of a catheter. It avoids the risks and costs associated with the repeated removal of the wire guide for the catheter, and the cutting of the catheter to any specific length. The grommet positioner of the present invention is of simple and relatively inexpensive construction. Of course, the grommet positioner of the present invention is useful for positioning grommets on objects besides catheters.

Any undisclosed or incidental details of the construction or composition of the various elements of the disclosed embodiment of the present invention are not believed to be critical to the achievement of the advantages of the present invention, so long as the elements possess the characteristics needed for them to perform as disclosed. The selection of these and other details of construction are believed to be well within the ability of one of even rudimentary skills in this area, in view of the present disclosure.

INDUSTRIAL APPLICABILITY

The present invention is useful in performing surgical procedures, and therefore finds applicability in human and veterinary medicine.

It is to be understood, however, that the above-described device is merely an illustrative embodiment of the principles of this invention, and that other devices and methods for using them may be devised by those skilled in the art, without departing from the spirit and scope of the invention. It is also to be understood that the invention is directed to embodiments both comprising and consisting of the disclosed parts.

What is claimed is:

1. A device (10) for selectively positioning and fixing a grommet (14) on a catheter (12), comprising:

an elastic grommet (14) having a predefined, unstressed interior diameter about no greater than an outer diameter of a catheter (12) on which the grommet (14) is to be selectively positioned and fixed therealong; and a positioning member (16) carrying the grommet (14) thereon, the member (16) including a portion (25) in contact with the grommet (14);

wherein the portion (25) of the member (16) has an outer diameter at least equal to the predefined, unstressed interior diameter of the grommet (14);

wherein the positioning member (16) and the grommet (14) are selectively positionable together along the catheter (12); and wherein the member (16) is capable of being split along at least the portion (25), so as to release the grommet (14) from the member (16) and thereby fix the position of the grommet (14) at a selected position on the catheter (12).

2. The device (10) according to claim 1, wherein the positioning member (16) further comprises at least one pull tab (46) for splitting at least the portion (25) of the positioning member (16).

3. The device (10) according to claim 1, wherein the positioning member (16) is composed of molecular oriented PTFE.

4. The device (10) according to claim 1, wherein the positioning member (16) is capable of being split along its entire length.

5. The device (10) according to claim 1, wherein the grommet (14) comprises means (18) for assisting securement of the grommet (14) adjacent to the body (20) of a patient.

6. The device (10) according to claim 5, wherein the securement assisting means (18) comprises at least one ring (22).

7. The device (10) according to claim 5, wherein the securement assisting means (18) comprises at least one wing (24).

8. The device (10) according to claim 5, wherein the securement assisting means (18) comprises at least one shoulder (44).

9. The device (10) according to claim 5, wherein the securement assisting means (18) comprises a DACRON cuff (23).

10. The device (10) according to claim 1, wherein the grommet (14) is composed of silicone.

11. The device (10) according to claim 1, wherein the positioning member (16) comprises a sheath (28).

12. A device (10) for selectively positioning and fixing a grommet (14) On a catheter (12), comprising:

an elastic silicone grommet (14) having a predefined, unstressed interior diameter about no greater than an outer diameter of a catheter (12) on which the grommet (14) is to be selectively positioned and fixed therealong, the grommet (14) comprising a pair of shoulders (44) for assisting securement of the grommet (14) adjacent to the body (20) of a patient; and a positioning sheath (28) carrying the grommet (14) thereon, the sheath (28) including a portion (25)in contact with the grommet (14), and the portion (25) having an outer diameter greater than the predefined, unstressed interior diameter of the grommet (14);

wherein the positioning sheath (28) and the grommet (14) are selectively positionable together along the catheter (12); and wherein the sheath (28) is composed of molecular oriented PTFE and comprises a pair of pull tabs (46) for splitting the sheath (28) along its entire length so as to release the grommet (14) from the member (16) and thereby fix the position of the grommet (14) at a selected position on the catheter (12).

13. A catheterization apparatus (56), comprising:

a catheter (12) having an outer diameter;

an elastic grommet (14) encircling the catheter (12) and having a predefined, unstressed interior diameter about no greater than the outer diameter of the catheter (12); and a positioning member (16) received on the catheter (12) and carrying the grommet (14) thereon, the member (16) including a portion (25) in contact with the grommet (14), and the portion (25) of the member (16) having an outer diameter at least equal to the predefined, unstressed interior diameter of the grommet (14), so that the member (16) and the grommet (14) are selectively positionable together along the catheter (12);

wherein the member (16) is capable of being split along at least the portion (25), so as to release the grommet (14) from the member (16) and thereby fix the position of the grommet (14) at a selected position on the catheter (12).

14. The apparatus (56) according to claim 13, wherein the grommet (14) achieves an interference fit with the catheter (12) upon splitting of at least the portion (25) of the positioning member (16).

15. The apparatus (56) according to claim 13, wherein the grommet (14) achieves a compression fit with the catheter (12) upon splitting of at least the portion (25) of the positioning member (16).

16. The apparatus (56) according to claim 13, wherein the positioning member (16) comprises a sheath (28).

17. The apparatus (56) according to claim 13, wherein the positioning member (16) is composed of molecular oriented PTFE.

18. The apparatus (56) according to claim 13, wherein the positioning member (16) is capable of being split along its entire length.

19. The apparatus (56) according to claim 13, wherein the grommet (14) comprises means (18) for assisting securement of the grommet (14) adjacent to the body (20) of a patient.

20. The apparatus (56) according to claim 13, further comprising an obturator (34) removably received in the catheter (12).

21. The apparatus (56) according to claim 13, wherein the positioning member (16) further comprises at least one pull tab (46) for splitting at least the portion (25) of the positioning member (16).

22. The apparatus (56) according to claim 13, characterized in that friction against or compression of the catheter (12) by the grommet (14) is the sole force preventing relative movement of the grommet (14) and the catheter (12) after splitting of the positioning member (16).

* * * * *